United States Patent
Cowe

(10) Patent No.: US 8,647,303 B2
(45) Date of Patent: Feb. 11, 2014

(54) INJECTION DEVICES

(75) Inventor: Toby Cowe, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 466 days.

(21) Appl. No.: 12/866,621

(22) PCT Filed: Feb. 3, 2009

(86) PCT No.: PCT/GB2009/050097
§ 371 (c)(1),
(2), (4) Date: Aug. 6, 2010

(87) PCT Pub. No.: WO2009/098502
PCT Pub. Date: Aug. 13, 2009

(65) Prior Publication Data
US 2010/0324485 A1 Dec. 23, 2010

(30) Foreign Application Priority Data
Feb. 8, 2008 (GB) .................................. 0802351.7

(51) Int. Cl.
*A61M 5/20* (2006.01)
(52) U.S. Cl.
USPC .......................................... 604/134; 604/211
(58) Field of Classification Search
USPC .................. 604/208–211, 239, 248, 232–233, 604/235–236, 218, 221–223, 151, 132, 117
See application file for complete search history.

(56) References Cited

U.S. PATENT DOCUMENTS

| | | | |
|---|---|---|---|
| 2,309,502 | A | 1/1943 | Beverly |
| 3,797,488 | A | 3/1974 | Hurschman et al. |
| 4,313,439 | A | 2/1982 | Babb et al. |
| 5,261,882 | A | 11/1993 | Sealfon |

(Continued)

FOREIGN PATENT DOCUMENTS

| | | |
|---|---|---|
| DE | 10 2005 038933 | 2/2007 |
| DE | 10 2006 022081 | 1/2008 |

(Continued)

OTHER PUBLICATIONS

International Search Report, PCT/GB2009/050097, Oct. 9, 2009.

*Primary Examiner* — Theodore Stigell
*Assistant Examiner* — Melissa A Snyder
(74) *Attorney, Agent, or Firm* — Young & Thompson

(57) ABSTRACT

An autoinjector device comprises a drive housing 10 and a syringe housing 12 which can be disconnected to allow insertion of a syringe. A drive mechanism in the drive housing is cocked by means of a cord 8 connected between the drive housing and the syringe housing. The drive mechanism comprises a drive gear 22 rotatably mounted in the drive housing and acting as a rotary crank connected by a connecting rod 26 to a plunger 28. In use the drive gear 22 is driven by a torsion spring 35 so that the drive mechanism extends the syringe from the syringe housing and expels a dose and then retracts the syringe back into the housing. A firing button 14 releases the drive gear to be driven by the torsion spring but is also engageable as a brake on the rim of the drive gear.

18 Claims, 5 Drawing Sheets

(56) References Cited

U.S. PATENT DOCUMENTS

| | | | |
|---|---|---|---|
| 5,865,804 A * | 2/1999 | Bachynsky | 604/134 |
| 5,899,879 A | 5/1999 | Umbaugh | |
| 6,149,626 A | 11/2000 | Bachynsky et al. | |
| 2001/0047151 A1 | 11/2001 | Xian et al. | |
| 2004/0054326 A1 | 3/2004 | Hommann et al. | |
| 2006/0106342 A1 | 5/2006 | Cox | |
| 2007/0043319 A1 | 2/2007 | Kimmel et al. | |

FOREIGN PATENT DOCUMENTS

| | | |
|---|---|---|
| FR | 2 884 723 | 10/2006 |
| GB | 2 388 033 | 11/2003 |
| GB | 2 438 629 | 12/2007 |
| WO | WO 96/28202 | 9/1996 |

* cited by examiner

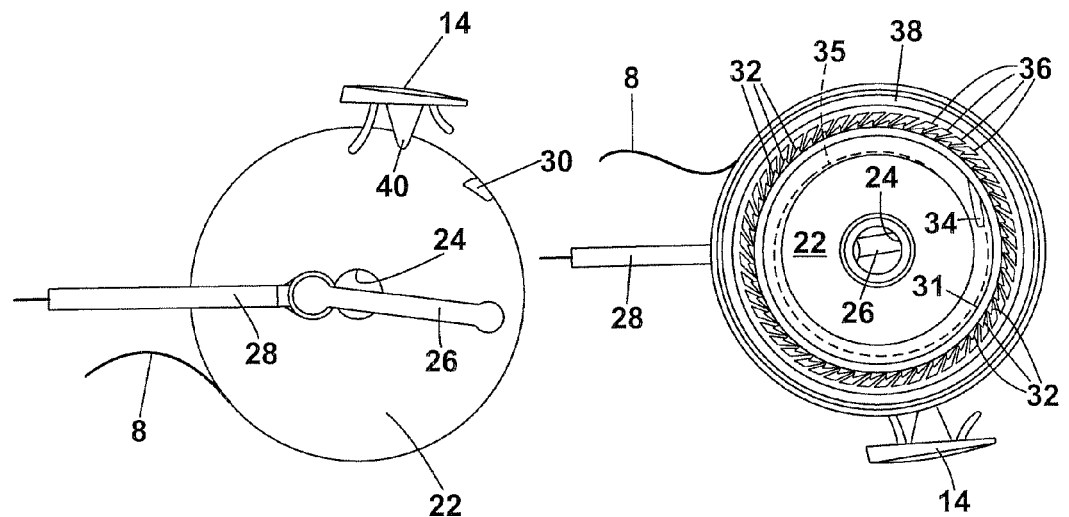
*Fig. 5*  *Fig. 6*
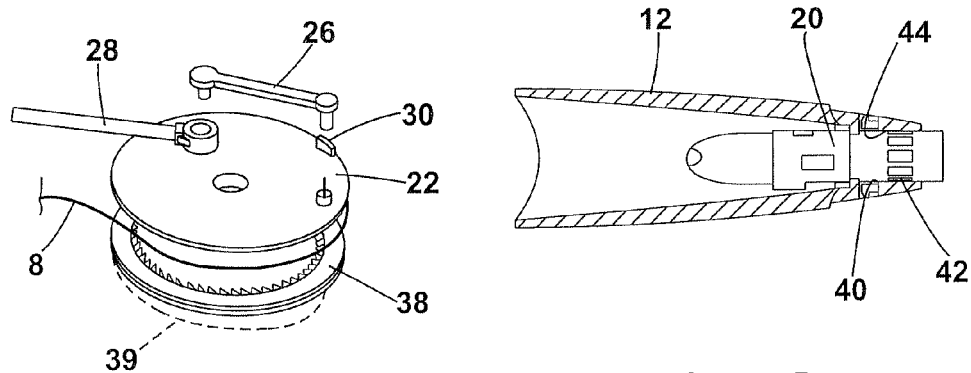
*Fig. 7*  *Fig. 8*

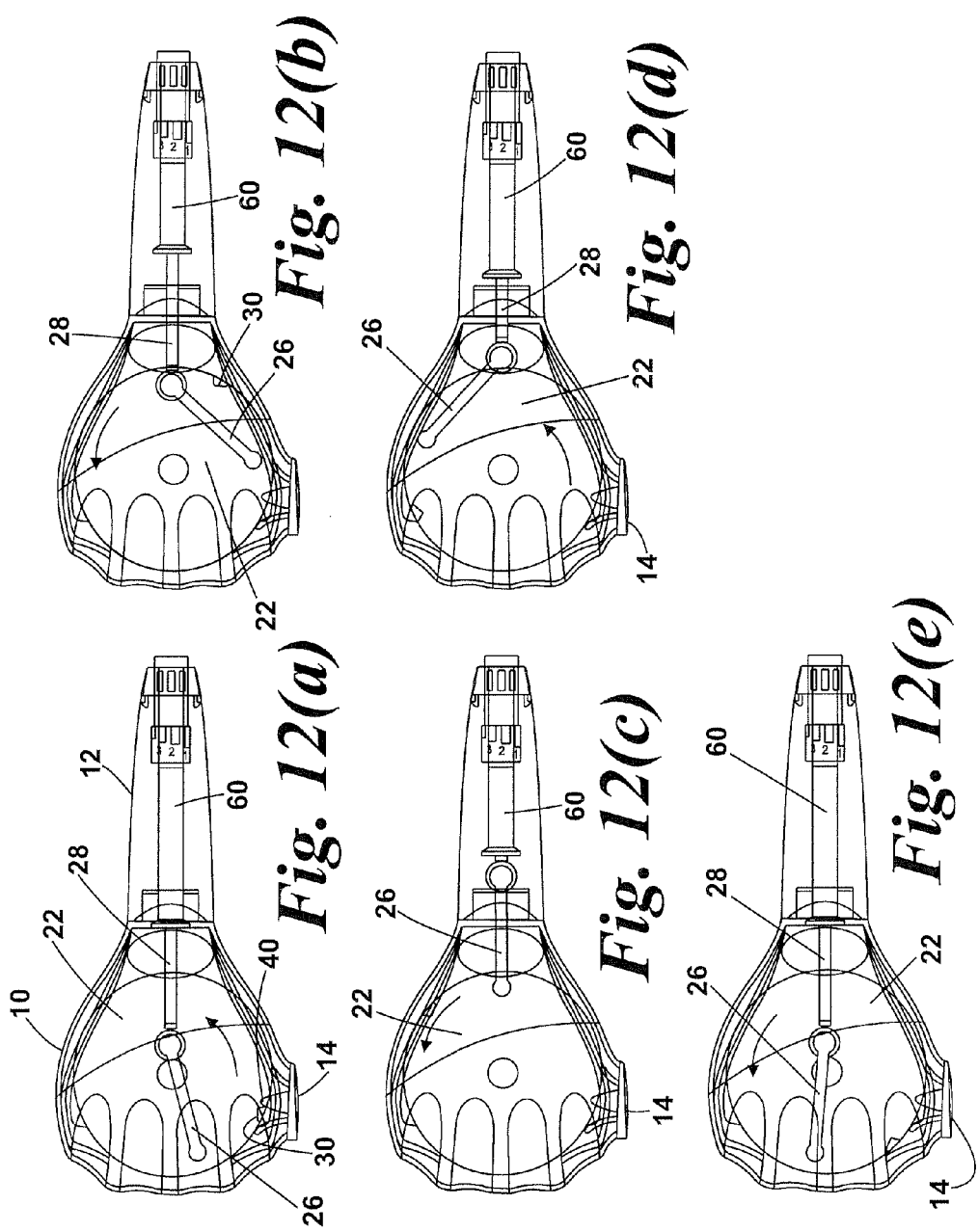

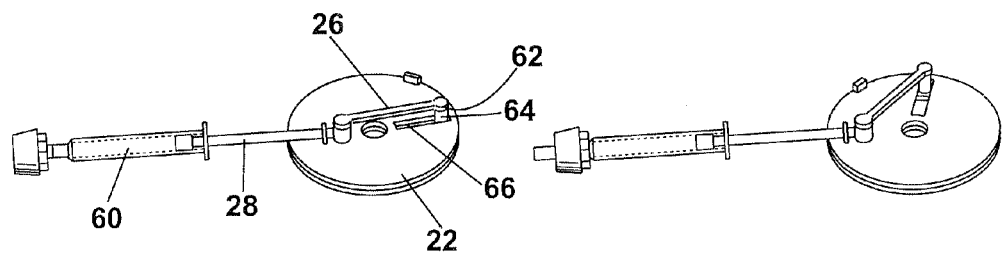
*Fig. 13(a)*  *Fig. 13(b)*
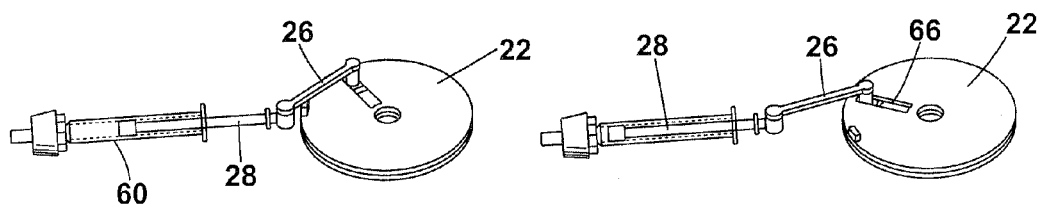
*Fig. 13(c)*  *Fig. 13(d)*
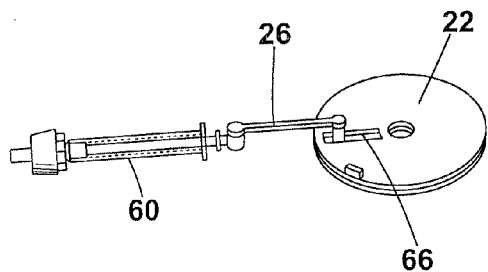 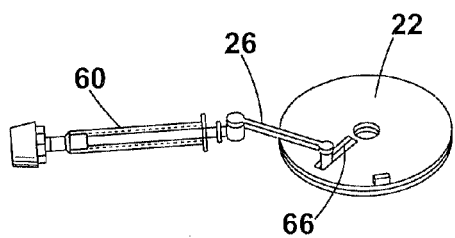
*Fig. 13(e)*  *Fig. 13(f)*

INJECTION DEVICES

This invention relates to autoinjection devices and injection devices generally. In particular, but not exclusively, the invention is concerned with autoinjection devices which are designed for multiple use.

Such devices may be used where it is required to autoinject on a regular basis a dose of medicament which is contained in a disposable syringe or a cartridge. In the majority of, if not all, such devices it is necessary to cock the drive mechanism of the device in some way to energise an energy storage device e.g. a spring. Once cocked, firing the drive mechanism causes the syringe or cartridge to be advanced so that the needle penetrates the skin of a user whereupon the dose is expelled. A problem with such devices is that, to ensure that there is sufficient stored energy in the device to effect these operations in a swift and reliable manner, a significant force has to be applied. This is problematic for those who are weak or with reduced manual dexterity. Also there is a risk that if the device slips during the cocking operation, injury could be caused.

Therefore a need exists for a injection device with a cocking process that overcomes at least some of these disadvantages.

SUMMARY OF THE INVENTION

Accordingly, in one aspect, this invention provides an autoinjector comprising:
  a body portion for receiving in use a syringe or cartridge having a bung slideably mounted therein for expelling a dose;
  a drive mechanism including energy storage means and adapted to be released from a cocked position to a fired position on actuation of a trigger, said mechanism when released being operable to drive the bung to expel a dose, characterised by a cocking arrangement comprising an elongate flexible element for being pulled by hand to cock said drive mechanism.

Cocking the device by pulling an elongate flexible element by hand has the advantage that the pulling operation tends to be easier to achieve by those with a weak grip or reduced dexterity and slippage is less likely to cause difficulty.

Optionally the drive mechanism is also operable to move said syringe or cartridge forwardly in said body portion to an injection position and to retract it.

Preferably, the cocking arrangement includes a mechanical advantage configuration whereby the stroke of movement of said elongate flexible element is substantially greater than the stroke of movement of said drive mechanism. In this way, a more gentle cocking force can be applied over a greater distance whilst still providing sufficient energising of the energy storage means or spring.

Conveniently, the cocking arrangement includes retraction means for retracting the elongate flexible element after the drive mechanism has been cocked. This ensures that the elongate flexible element is stored out of the way to avoid snagging.

Although the drive mechanism may take many forms, it is particularly preferred for it to comprise a rotary crank element connected to a slideable drive plunger by a connecting rod in a crank-slider relationship, with the energy storage means acting on the rotary element. The energy storage means may for example be a torsion spring. This provides several important advantages. The rotary crank element can provide an injection cycle where there is a dwell at the further stroke of the drive plunger to allow the bung to re-expand before the mechanism retracts the syringe. It also allows significant mechanical advantage because the elongate flexible element can be wrapped around the periphery of a relatively large diameter rotary element.

Thus the cocking arrangement preferably includes a rotary cocking element or pulley around which the elongate flexible element is wrapped, with there being a clutch arrangement for transmitting rotation to said rotary crank element in the cocking sense only, and means for rewinding the cocking element or pulley after cocking to attract the elongate flexible element.

A further advantage and a preferred embodiment is that a surface of the rotary cocking element can be used as a brake surface. Accordingly, in a preferred arrangement, the release trigger for the drive mechanism is further operable to apply or modulate a braking force on the drive mechanism to allow control of the speed of movement thereof from said cocked position, and thereby the speed of movement of the syringe/cartridge and/or bung.

Where the device needs to have a new syringe or cartridge fitted at regular intervals or before each dose, it is particularly preferred for the body portion to comprise a forward portion for receiving the syringe or cartridge and a rearward portion removably connected to the forward position and housing said drive mechanism. In this arrangement, it is particularly convenient for the elongate flexible element to extend from the rearward portion to a connection on the forward portion. The connection on the forward portion may allow limited sliding movement of the elongate flexible element against a slight bias whereby on initial separation of the forward and reward portion to allow internal access for the removable/insertion of a syringe or cartridge, there is a degree of "slack" before the drive mechanism begins to be energised.

It is known to have a penetration depth adjustment facility on an injection device to allow the injection depth to be varied. Typically these comprise a collar at the forward end of the device which needs to be rotated by hand until the correct depth has been dialled in. These are relatively small in diameter and often protrude only a short distance from the housing and so are not particularly convenient to adjust.

Preferably therefore the autoinjector includes a penetration depth adjustment element disposed in a forward end of the body portion and for being placed against the injection site in use, the adjustment element being connected to a depth adjustment mechanism for advancing and/or retracting said adjustment element incrementally relative to said body portion upon manual actuation of a separate depth adjustment actuator. In one arrangement, the adjustment element is threadedly mounted on the body portion and the depth adjustment mechanism comprises as least one push button cooperating with the adjustment element incrementally to rotate said adjustment element upon each actuation of the button. The term threadedly mounted is used broadly as meaning any arrangement where, at least over part of an arc of rotation, rotation of the adjustment element causes linear movement thereof relative to the housing. Preferably, the arrangement includes two push buttons disposed on opposite sides of the body portion, each cooperating with said depth adjustment element. This means that the depth adjustment element can be incrementally used by the user pinching the push buttons which is a relatively easy operation.

The push button and the adjustment element preferably cooperate by means of a ratchet surface on one and a pawl on the other. Preferably, the engagement between the depth adjustment element and the body portion is such that, when the depth adjustment element reaches a preset longitudinal extent of movement, further incremental movement thereof causes the depth adjustment element to return to a start position.

In another aspect, this invention provides an autoinjector comprising:
a body portion for receiving in use a syringe or cartridge having a bung slideably mounted therein for expelling a dose;
a drive mechanism including energy storage means and adapted to be released from a cocked position to a fired position on actuation of a trigger, said mechanism when released being operable to drive the bung to expel a dose,
characterised in that said drive mechanism includes a rotary crank element connected to a slideable drive plunger by a connecting rod in a crank-slider relationship, and said energy storage means acts on said rotary crank element.

In yet another aspect, the invention provides an autoinjector comprising:
a body portion for receiving in use a syringe or cartridge having a bung slideably mounted therein for expelling a dose;
a drive mechanism including energy storage means and adapted to be released from a cocked position to a fired position on actuation of a trigger, said mechanism when released being operable to drive the bung to expel a dose,
characterised in that said drive mechanism includes user operable means for applying or modulating a braking force to control the speed of operation of said mechanism.

In a further aspect, the invention provides a penetration depth adjustment arrangement for an injection device, said arrangement comprising:
a housing having a forward end region through which the injection is effected;
a depth adjustment element disposed in said forward end region and for being placed against the injection site in use, and
a depth adjustment mechanism for advancing and/or retracting said adjustment element incrementally relative to said housing upon manual actuation of a separate depth adjustment actuator.

Whilst the invention has been described above, it extends to any inventive combination of the features set out above or in the following description.

BRIEF DESCRIPTION OF THE DRAWINGS

The invention may be formed in various ways, and an embodiment thereof will now be described by way of example only, reference being made to the accompanying drawings in which:

FIG. 5 is a side view of the cranked drive mechanism with the housing removed;
FIG. 6 is a view similar to FIG. 5 but from the opposite side;
FIG. 7 is an exploded view of the components making up the cranked drive mechanism;
FIG. 8 is a section view through the forward end of the syringe housing showing the depth adjustment collar;
FIGS. 12$j(a)$ to $(e)$ are views showing the crank mechanism at successive phases of the autoinjection cycle, and
FIGS. 13 $(a)$ to $(f)$ are views showing the crank mechanism at successive phases of the autoinjection cycle of a modified embodiment.

DETAILED DESCRIPTION OF THE PREFERRED EMBODIMENTS

Figure 1:
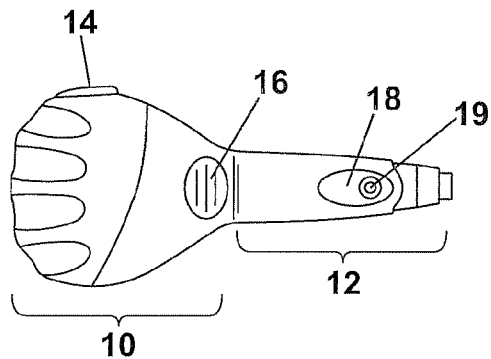
FIG. 1 is a top plan view of a autoinjector device in accordance with this invention, ready for operation.
Figure 2:
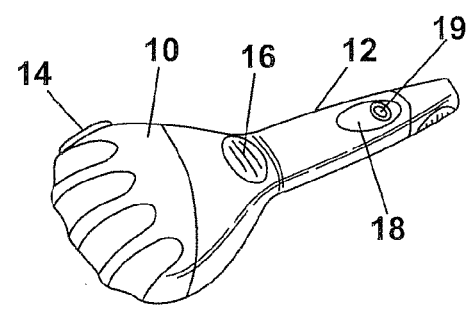
FIG. 2 is a perspective view of the device of FIG. 1.
Figure 3:
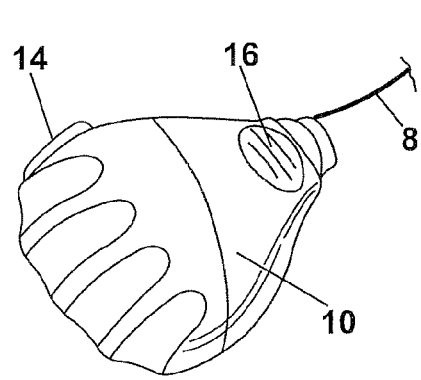
FIG. 3 is a view of the drive housing of the autoinjector.
Figure 4:
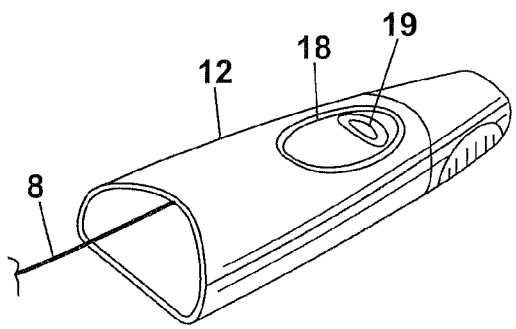
FIG. 4 is a view of the syringe housing of the autoinjector.
Figure 9:
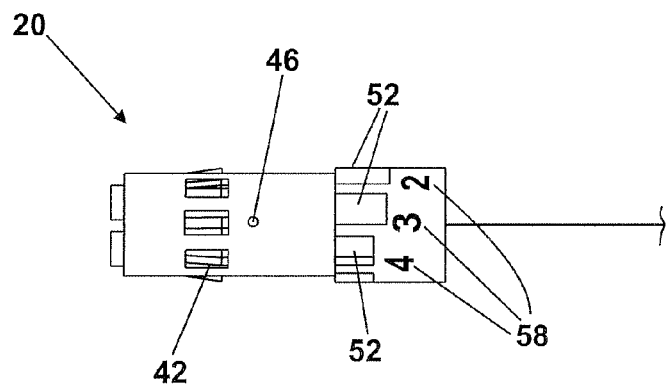
FIG. 9 is a side view of the depth adjustment collar.
Figure 10:
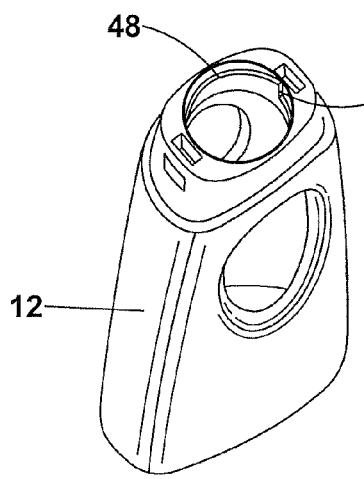
FIG. 10 is a perspective view on the forward end of the syringe housing showing the rising cam surface that cooperates with the depth adjustment collar.

The device illustrated in the drawings is intended to allow easy autoinjection of a medicament from a disposable syringe which is fitted into the device. The device is intended to be "broken" into two separate parts to both allow insertion of the syringe into the syringe housing but also to allow the drive mechanism in the drive housing to be cocked by means of a cord 8 connected between the drive housing and the syringe housing.

The device comprises a drive housing 10 which houses the drive mechanism to be described below and which is shaped to fit easily in the palm of a user. A firing button 14 projects from the drive housing. The drive housing attaches to the syringe housing by a click fit which may be released by depressing two release buttons 16 on the drive housing. The syringe housing is provided with diametrically opposed penetration depth adjustment buttons 18 which are used as described below to adjust the amount of axial projection of a penetration depth collar 20 from the forward end of the device. The penetration depth adjustment buttons 18 are apertured at 19 to allow the current depth setting to be read from the rearward surface of the penetration depth collar.

Referring now to FIGS. 5 to 7, the drive mechanism contained in the drive housing 10 comprises a drive gear 22 which is rotatably mounted in the drive housing by a central boss 24 and which acts as a rotary crank, being connected by means of a connecting rod 26 to a plunger 28 which is mounted in the device for longitudinal sliding movement. A trigger latch 30 is provided at the periphery of the drive gear 22. On its opposite face, the drive gear 22 has an upstanding annular rim 31 at about three quarters the radius of the drive gear 22, on the radially outer surface of which are ratchet teeth 32. On the radially inner surface of the annular rim 30 there is an anchorage point 34 for a torsion spring 35 the other end of which is anchored to the housing at an anchorage (not shown). The ratchet teeth 32 cooperate with corresponding sprung pawls extending radially inwardly from a cord pulley 38. The ratchet teeth 34 and pawls cooperate such that rotation of the cord pulley 38 counter clockwise as viewed in FIG. 6 is transmitted to the drive gear 22 to wind up the drive gear torsion spring but the drive gear is free to rotate clockwise relative to the cord pulley 38. As the drive gear is rotated to its fully energised position the trigger latch 30 on the drive gear latches behind a projection 40 on the firing button 14, to latch the drive mechanism in its energised position. Releasing the tension on the cord 8 allows the cord pulley to rewind the cord under the influence of the further torsion spring 39 acting between the cord pulley and the housing.

Figure 11:
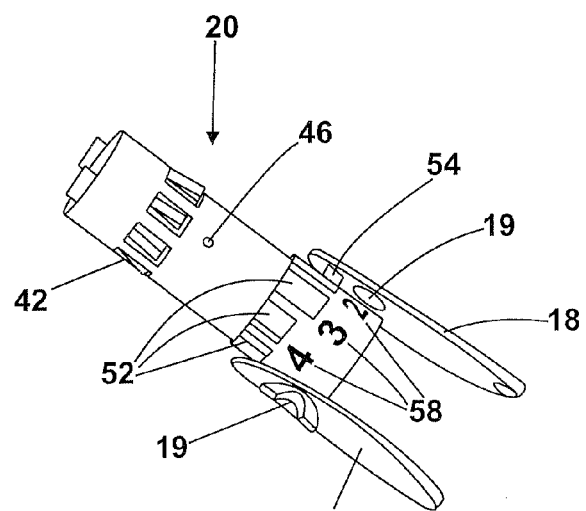
FIG. 11 is an exploded view of the depth adjustment collar and diametrically opposed actuating buttons.

Referring now to FIGS. 8 to 11, the syringe housing 12 receives at its forward end the penetration depth adjustment collar 20 for rotation. Projecting radially from the forward end of the collar are a number of sprung tangs 42 that engage one or more corresponding recesses 44 in the forward end of the syringe housing to provide a click detent action to define incremental angular movement. To the rear of the tangs 42 are two diametrically opposed protruding pegs 46 which engage corresponding rising cam surfaces 48 in the forward end of the housing (see FIG. 10). The rising cam surfaces 48 terminate with a step 50 to provide a saw-toothed profile. The rear end of the collar 20 has a forward facing shoulder engaged by a spring (not shown) to bias the collar rearwardly, and the pegs 46 into contact with the rising cam surfaces 48. Around the periphery of the rear of the collar is provided a series of ratchet recesses 52 of progressively increasing axial extent. As shown in FIG. 11, the penetration depth adjustment buttons 18 have sprung pawls 54 which engage the recesses 52. When assembled, pressing the penetration depth adjustment buttons 18 towards each other causes the collar to rotate one increment which causes the collar to advance incrementally out of the housing. Indicia 58 on the collar are visible through apertures 19 in the adjustment buttons 18 to indicate to the user the depth set.

In operation, the housing is opened into its separate parts by depressing buttons 16 and a spent syringe (if present) can be removed and replaced by a new syringe 60. The drive housing 10 is then pulled away from the syringe housing so that the cocking cord 8 is pulled to rotate the cord pulley and thus wind up the drive gear against the bias of the torsion spring, until the trigger latch 30 latches behind the projection 40 on the trigger. The drive housing and syringe housings are then re-assembled so as to place the various elements in the configuration shown in FIG. 12 (*a*).

Pressing the firing button 14 releases the drive gear 22 so that it can rotate counter clockwise (as viewed in FIG. 12) and forward movement is imparted to the plunger 28 which causes the syringe 60 to move forwardly and project its needle out of the forward end of the drive housing. Continued rotation of the drive gear then advances the plunger further so that it drives the syringe bung to expel a dose and this continues until the dead centre position shown in FIG. 12 (*c*). As indicated previously, this provides a dwell position to allow the bung to re-expand. Thereafter the plunger 28 retracts, pulling the syringe 60 with it to withdraw the needle back into the housing with the drive gear 22 coming to rest at or near the other dead centre position.

The firing button 14 also has a dual function in that it is designed to act as a brake on the periphery of the drive gear so as to give the user control over the speed with which the autoinjection cycle is executed. This can be useful because some medicaments are painful to inject and it provides a useful degree of control for the user. The braking effect may simply be friction between the button and the periphery of the drive gear, so that pressing the firing button 14 when the mechanism is in movement applies a retarding effect. It is also possible to have the opposite arrangement whereby releasing the button provides a braking effect, and pressing it removes the braking effect.

Referring to FIGS. 13 (*a*) to (*f*), in this modification the mounting between the connecting rod 26 and the drive gear 22 permits limited sliding movement or lost motion. The connecting rod 28 is coupled to a peg 62 on a block 64 which slides in a slot 66 on the drive gear against a radial outward bias provided by a spring (not shown) as the mechanism moves to the position where the plunger is fully extended (FIG. 13(*d*)). Any mismatch of axial tolerances due to the glass syringe is accommodated by the lost motion device thereby ensuring that the dose is fully expelled and that stalling of the drive mechanism is prevented.

The invention claimed is:

1. An autoinjector, comprising:
   a body portion (12) for receiving in use a syringe or cartridge (60) having a bung slideably mounted therein for expelling a dose;
   a drive mechanism (35, 22, 26, 28) including a stored energy device (35) and adapted to be released from a cocked position to a fired position on actuation of a trigger (14), said mechanism when released being operable to drive the bung to expel a dose; and
   a cocking arrangement (8, 30, 40), comprising an elongate flexible element (8) configured to be pulled to energize said drive mechanism in order to cock said drive mechanism into a mode ready for subsequent release by said trigger
   wherein said cocking arrangement includes a mechanical advantage configuration (38, 8) whereby a stroke of movement of said elongate flexible member (8) is substantially greater than a stroke of linear movement of said drive mechanism.

2. The autoinjector according to claim 1, wherein said cocking arrangement includes retraction arrangement (39) for retracting said elongate flexible element (8) after said drive mechanism has been cocked.

3. The autoinjector according to claim 1, wherein said drive mechanism comprises a rotary crank element (22) connected to a slideable drive plunger (28) by a connecting rod (26) in a crank-slider relationship, and said stored energy device (35) acts on said rotary crank element (22).

4. The autoinjector according to claim 3 including a lost motion connection (64, 66) between at least two out of the rotary crank element (22), the connecting rod (26) and the drive plunger (28).

5. The autoinjector according to claim 3, wherein said stored energy device (35) comprises a torsion spring connected at one end to said rotary element and relatively fixed at its other end.

6. The autoinjector according to claim 5, wherein said cocking arrangement comprises a rotary element, or pulley (38) around which is wrapped said elongate flexible cocking element (8) and a clutch arrangement (32, 36) for transmitting rotation to said rotary crank element in the cocking sense only, and an arrangement (39) for rewinding said clocking element or pulley after cocking to retract said elongate flexible element.

7. The autoinjector according to claim 1, wherein said trigger (14) is operable to apply or modulate a braking force on said drive mechanism to allow control of the speed of movement thereof from said cocked position, and thereby the speed of movement of at least one of the syringe or cartridge and bung.

8. The autoinjector according to claim 1, wherein said body portion comprises a forward portion (12) for receiving said syringe or cartridge, and a rearward portion (10) removably connected to said forward portion and housing said drive mechanism.

9. The autoinjector according to claim 8, wherein said elongate flexible element (8) extends from said rearward portion (10) to a connection on said forward portion (12).

10. The autoinjector according to claim 9, wherein the connection on said forward portion allows sliding movement of said elongate flexible element (8) for a preset distance against a slight bias, whereby on initial separation of said forward and rearward portions, said elongate flexible cocking element (8) moves longitudinally relative to said forward portion.

11. The autoinjector according to claim 1 including a penetration depth adjustment element (20) disposed in a forward end of the body portion (12) and for being placed against the injection site in use, said adjustment element being connected to a depth adjustment mechanism for advancing and/or retracting said adjustment element incrementally relative to said body portion upon manual actuation of a separate depth adjustment actuator (18).

12. The autoinjector according to claim 11, wherein said adjustment element (20) is threadedly mounted on said body portion (12), and said depth adjustment mechanism comprises at least one push button (18) cooperating with said adjustment element incrementally to rotate said adjustment element upon each actuation of said button.

13. The autoinjector according to claim 12, including push buttons (18) disposed on opposite sides of said body portion, each cooperating with said depth adjustment element (20).

14. The autoinjector according to claim 12, wherein the or each push button (18) and said adjustment element (20) cooperate by means of a ratchet and pawl.

15. The autoinjector according to claim 11, wherein said depth adjustment mechanism is operable on said depth adjustment element reaching a preset longitudinal position (20), to return said depth adjustment element to a start position.

16. An autoinjector, comprising:
a body portion (10,12) for receiving in use a syringe or cartridge (60) having a bung slideably mounted therein for expelling a dose; and
a drive mechanism including a stored energy device (35) and adapted to be released from a cocked position to a fired position on actuation of a trigger (14), said mechanism when released being operable to drive the bung to expel a dose, said drive mechanism including
a rotary crank element (22) rotatable about a rotary axis,
a slideable drive plunger (28) displaceable along a drive axis, and
a connecting rod (26) pivotally coupled to said rotary crank element and said slideable drive plunger in a crank-slider relationship,
wherein said stored energy device (35) is configured to act on said rotary crank element.

17. An autoinjector, comprising:
a body portion (10, 12) for receiving in use a syringe or cartridge (60) having a bung slideably mounted therein for expelling a dose; and
a drive mechanism including stored energy device (35) and adapted to be released from a cocked position to a fired position on actuation of a trigger (14), said mechanism when released being operable to drive the bung to expel a dose,
wherein said drive mechanism includes a user operable arrangement (14) for applying or modulating a braking force to control the speed of operation of said mechanism.

18. The autoinjector according to claim 1, wherein said cocking arrangement includes a retraction arrangement (39) for retracting said elongate flexible element (8) after said drive mechanism has been cocked.

* * * * *

UNITED STATES PATENT AND TRADEMARK OFFICE
CERTIFICATE OF CORRECTION

PATENT NO. : 8,647,303 B2
APPLICATION NO. : 12/866621
DATED : February 11, 2014
INVENTOR(S) : Toby Cowe It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 467 days.

Signed and Sealed this
Twenty-ninth Day of September, 2015

Michelle K. Lee
*Director of the United States Patent and Trademark Office*